:::
United States Patent [19]

Gresser et al.

[11] Patent Number: 5,817,328
[45] Date of Patent: Oct. 6, 1998

[54] MATERIAL FOR BUFFERED RESORBABLE INTERNAL FIXATION DEVICES AND METHOD FOR MAKING SAME

[75] Inventors: Joseph D. Gresser, Brookline; Debra J. Trantolo, Princeton; Robert Langer; Alexander M. Klibanov, both of Newton; Donald L. Wise, Belmont, all of Mass.

[73] Assignee: Cambridge Scientific, Inc., Belmont, Mass.

[21] Appl. No.: 626,521

[22] Filed: Apr. 3, 1996

Related U.S. Application Data

[63] Continuation-in-part of Ser. No. 587,616, Jan. 17, 1996, abandoned.

[51] Int. Cl.$^6$ .............................. A61F 2/02; A61K 47/30; A61K 47/32
[52] U.S. Cl. .................. 424/426; 514/772.1; 514/772.3; 514/772.4
[58] Field of Search ......................... 424/426; 514/772.1, 514/772.3, 772.4

[56] References Cited

U.S. PATENT DOCUMENTS

| | | | |
|---|---|---|---|
| 4,637,931 | 1/1987 | Schmitz | 424/78 |
| 4,780,319 | 10/1988 | Zentner et al. | 424/476 |
| 5,336,505 | 8/1994 | Ng et al. | 424/486 |
| 5,397,572 | 3/1995 | Combes et al. | 424/426 |
| 5,502,092 | 3/1996 | Barrows et al. | 521/64 |

*Primary Examiner*—Carlos Azpuru
*Attorney, Agent, or Firm*—Weingarten, Schurgin, Gagnebin & Hayes LLP

[57] ABSTRACT

A bioerodible implantable material, comprising a bioerodible polymer that produces acidic products upon hydrolytic degradation, and a buffering compound that buffers the acidic products and maintains the local pH within a desired range. The buffer compound acts to reduce the inflammatory foreign body response generated by the acidic products and reduces the sterile abscess condition that occurs at the site of the bioerodible implant materials of the prior art. Materials made according to the invention may be used for internal fixation devices (IFDs) for bone repair.

61 Claims, No Drawings

MATERIAL FOR BUFFERED RESORBABLE INTERNAL FIXATION DEVICES AND METHOD FOR MAKING SAME

CROSS-REFERENCE TO RELATED APPLICATIONS

This application is a continuation-in-part of U.S. application Ser. No. 08/587,616, filed Jan. 17, 1996, now abandoned.

FIELD OF THE INVENTION

This invention relates to the field of implantable internal fixation devices for repair of bone fractures, and more specifically to resorbable bone implant biomaterials which contain a buffering compound.

BACKGROUND OF THE INVENTION

The trend in internal fixation devices for repair of damaged bone is toward the use of resorbable, tissue compatible biopolymers. Biopolymers such as poly(glycolic acid) (PGA), poly(lactide) (PLA), and copolymers of lactic and glycolic acids, (poly(lactide-co-glycolide) or PLGA) have been used in the production of internal fixation devices, such as screws, pins, and rods to hold bone together following surgery, or to repair broken bones. Other polymers, such as poly(dioxanone), have also been considered for use in the manufacture of surgical internal fixation devices. However, it has been observed that tissue response to resorbable implants fabricated from these biopolymers is not uniformly acceptable (Bostman, J. Bone and Joint Surg. 73, 148–153 (1991)).

The tissue response to biopolymer-based implants has been well documented. Late sterile inflammatory foreign body response (sterile abscess) has been reported in about 8% of fractures repaired with these polymers (Bostman, supra). In a randomized study of 56 open reduction and internal fixation of malleolar fractures of the ankle with metal ASIF screws and plates or with rods of PLGA, two cases of sterile inflammatory wound sinus were observed 3 to 4 months after the operation in the injuries fixed with the polymer rods (Rokkanen et al., Lancet 1, 1422–1425 (1985); Bostman et al., J. Bone and Joint Surg., 69-B(4), 615–619 (1987)). Other studies have also documented an inflammatory reaction following implantation of PGA or PLGA fixation devices. The fraction of patients suffering from this reaction ranges from 4.6 to 22.5% (Bostman et al., Clin. Orthop. 238, 195–203 (1989); Bostman et al., Internat. Orthop. 14, 1–8 (1990); Hirvensalo et al., Acta Orthop. Scandinavica, Supplementum 227, 78–79 (1988); Hoffman et al., Unfallchirurgie 92, 430–434 (1989); Partio et al., Acta Orthop. Scandinavica, Supplementum 237, 43–44 (1990); Bostman et al., Internat. Orthop. 14, 1–8 (1990)). The inflammatory reaction is not limited to poly(glycolide) polymers. Internal fixation devices made from poly(lactide) have also been observed to exhibit an inflammatory reaction. Eitenmuller et al. reports that 9 of 19 patients (47.7%) who had fractures of the ankle treated with absorbable plates and screws of poly(lactide) had an inflammatory response. (J. Eitenmuller, A. David, A. Pomoner, and G. Muhyr: "Die Versorgung von Sprunggelenlzsfrakturen unter Verwendung von Platten und Schrauben aus resorbserbarem Polymermaterial", Read at Jahrestagung der Deutschen Gesellschaft fur Unfallheilkunde, Berlin, Nov. 22, 1989).

In vitro studies have been performed to monitor pH changes as well as weight loss and the appearance of lactic acid from screws fabricated from poly(lactide-co-glycolide) with a lactide:glycolide ratio of 85:15. (Vert et al., J. Controlled Release 16, 15–26 (1991)). An induction period of about ten weeks was observed before any significant change in media pH or weight loss occurred. This time period corresponds to the induction periods of seven to twenty weeks noted by clinicians. However, no attempt has been made to alleviate the source of inflammation.

SUMMARY OF THE INVENTION

The invention is a bioerodible implantable material, comprising a bioerodible polymer that produces acidic products upon hydrolytic degradation, and a buffering compound that buffers the acidic products and maintains the local pH within a desired range. The buffer compound incorporated into the material of the invention acts to neutralize the acidic degradation products which cause inflammatory foreign body response upon degradation of the bioerodible polymer. Thus, the invention reduces the sterile abscess condition that occurs in the bioerodible implant materials of the prior art. Materials made according to the invention may be used for internal fixation devices (IFDs) for bone repair.

The bioerodible materials and methods of the invention include a bioerodible polymer that forms acidic products as it degrades. The bioerodible polymer undergoes hydrolysis in the body and generates acidic products that cause irritation, inflammation, and swelling (sterile abscess formation) in the treated area. To counteract this effect, a buffer is included in the bioerodible material to neutralize the acidic degradation products and thereby reduce the sterile abscess reaction. The buffer included in the bioerodible material of the invention maintains the pH surrounding the area of surgery to approximately neutrality (i.e., pH 7), or any other pH chosen by the surgeon. Preferably, the pH is maintained in the range of 6–8, and more preferably in the range of 6.8–7.4.

According to the invention, the bioerodible material includes a bioerodible polymer that undergoes hydrolysis to produce acidic products when exposed to an aqueous medium. The bioerodible polymers useful in the invention include polydioxanone, poly($\epsilon$-caprolactone); polyanhydrides; poly(ortho esters); copoly(ether-esters); polyamides; polylactones; poly(propylene fumarates) (H[—O—CH(CH$_3$)—CH$_2$—O-CH=CH—CO—]$_n$OH); and combinations thereof. In a preferred embodiment, the polymer poly(lactide-co-glycolide) (H[—OCHR—CO—]$_n$OH, R=H, CH$_3$) (PLGA) is used. The PLGA polymers used according to the invention have a lactide to glycolide ratio in the range of 0:100% to 100:0%, inclusive, i.e., the PLGA polymer can consist of 100% lactide, 100% glycolide, or any combination of lactide and glycolide residues. These polymers have the property of degrading hydrolytically to form lactic and glycolic acids.

The buffering compound included in the bioerodible material of the invention may be any base or base-containing material that is capable of reacting with the acidic products generated upon hydrolysis of the bioerodible polymer. Exemplary buffering materials that may be implemented according to the invention include the salts of inorganic acids, the salts of organic acids, or the salts of polymeric organic acids. Preferably, the calcium salts of weak acids are used, such as calcium carbonate, although calcium phosphates, calcium acetates, calcium citrates and calcium succinates may also be used.

Polymeric buffers may also be used as buffering compounds according to the invention. Suitable polymeric buffers preferably include basic groups which neutralize the acidic products generated upon hydrolysis of the bioerodible polymer. Such polymeric buffers include hydrolyzable polyamines, hydrolytically stable polymers, such as poly(N-vinyl carbazole), poly(N-vinyl pyrrolidone), poly(acrylic acid), poly(acrylamide), or a copolymer based on acrylic acid.

Another class of buffering compounds useful in the materials and methods of the invention are compounds which, on exposure to water, hydrolyze to form a base as one reaction product. The generated base is free to neutralize the acidic products produced upon hydrolysis of the bioerodible polymer. Compounds of this type include aryl or alkyl carbamic acids and imines. The base-generating compounds used according to the invention offer the advantage that the rate of hydrolysis of the base generator may be selected to correlate to the rate of hydrolysis of the bioerodible polymer.

Preferably, the buffering compound has an acid dissociation constant that is smaller than the acid dissociation constant of the acidic products generated upon hydrolysis of the bioerodible polymer. Alternatively, the buffering compound preferably has a hydrolysis constant that is greater than the hydrolysis constant of the acidic products.

Preferably, the buffering compound included in the material of the invention is only partially soluble in an aqueous medium. In general, buffers of lower solubility are preferred because buffer loss from the polymer by diffusion will be minimized (Gresser and Sanderson, "Basis for Design of biodegradable Polymers for Sustained Release of Biologically Active Agents" in *Biopolymeric Controlled Release Systems*, Ch. 8, D. L. Wise, Ed., CRC Press, 1984).

The invention also includes methods of making a buffered bioerodible material for implantation into a surgical site. In one embodiment, the method according to the invention includes the steps of dissolving a bioerodible polymer in a solvent, and mixing a buffering compound with the dissolved bioerodible polymer, the buffering compound capable of buffering the acidic products within a desired pH range. The resulting mixture is cast into a sheet, and the solvent is evaporated to produce a buffered bioerodible implantable material in film form. The resulting film may be further processed, for example, compacted under pressure, extruded through a die, injection molded, or shaped into a form useful for bone repair.

In another embodiment, the method according to the invention includes mixing dry, solid bioerodible polymer particles of a specific size with dry, solid buffering compound particles of a specific size, and mixing the bioerodible polymer particles and the buffering compound particles in a desired proportion. This mixture may then be processed as described above.

In another embodiment, the method of the invention includes providing an open celled bioerodible foam polymer of controlled density and providing a buffer dissolved in a solvent wherein the foam polymer is not soluble in the solvent, such as described in U.S. Pat. No. 5,456,917 to Wise et al., the whole of which is incorporated by reference herein. The buffer is loaded into the foam polymer, and the loaded foam polymer is freeze dried to remove the solvent. The resulting loaded bioerodible polymer may be further ground into particles of a predetermined size, extruded through a die, or shaped into useful forms.

In another embodiment, the method of the invention includes providing a bioerodible polymer having a melting temperature and producing acidic products upon hydrolytic degradation, providing buffer particles comprising buffer material coated with a polymer having a melting temperature greater than the melting temperature of the bioerodible polymer. The bioerodible polymer is heated to a temperature between the melting temperatures of the bioerodible polymer and the coating polymer, and the heated bioerodible polymer is mixed with the coated buffer particles. The mixture is then cooled and processed into useful forms.

As used herein, the term "bioerodible" is defined as the susceptibility of a biomaterial to degradation over time, usually months. The term "buffer" is defined as any material which limits changes in the pH in the implant and its near environment only slightly upon exposure to acid or base. The term "acidic products" is defined herein as any product that has a pH less than 7.

DETAILED DESCRIPTION OF THE INVENTION

The invention relates to the field of internal fixation devices (IFD) used for surgical repair of orthopaedic and maxillofacial fractures. The invention is a bioerodible implantable material, comprising a bioerodible polymer capable of producing acidic products upon hydrolytic degradation, and a buffering compound that buffers the acidic products within a desired pH range.

The bioerodible material of the invention includes at least one bioerodible polymer that undergoes hydrolysis to produce acidic products when exposed to an aqueous medium. The bioerodible polymers useful in the invention include, but are not limited to, polydioxanone (H[—O—CHR—CO—]$_n$OH); poly($\epsilon$-caprolactone); polyanhydrides; poly(ortho esters); copoly(ether-esters); polyamides; polylactones; poly(propylene fumarates) (H[—O—CH(CH$_3$)—CH$_2$—O—CH=CH—CO—]$_n$OH); and combinations thereof. A preferred polymer material useful in the invention is poly(lactide-co-glycolide) (H[—OCHR—CO—]$_n$OH, R=H, CH$_3$) with a lactide to glycolide ratio in the range of 0:100% to 100:0%. Accordingly, the PLGA polymer can consist of 100% lactide, 100% glycolide, or any combination of lactide and glycolide. This polymer has the property of degrading hydrolytically to form organic acids (lactic acid and glycolic acid) which accumulate in the region surrounding the implant.

The buffering compound included in the bioerodible material of the invention includes base capable of reacting with the acidic products generated upon hydrolysis of the bioerodible polymer. Exemplary buffering materials that may be implemented according to the invention include the salts of inorganic acids, the salts of organic acids, or polymeric organic acids. Preferably, the calcium salts of weak acids are used, such as calcium carbonate, although calcium phosphates, calcium acetates, calcium citrates and calcium succinates may also be used.

In general, buffers of lower solubility are preferred because buffer loss from the polymer by diffusion will be slower (Gresser and Sanderson, supra). Preferably, the buffering compound has an acid dissociation constant that is smaller than the acid dissociation constant of the acidic products generated upon hydrolysis of the bioerodible polymer. Ionic buffers will, in general, be the salts of weak acids. The acid, of which the buffer is a salt, should have an ionization constant (acid dissociation constant, Ka) which is less than the Ka for the acid products of polymer hydrolysis. Alternatively, the buffering compound has a hydrolysis constant that is greater than the hydrolysis constant of the acidic products.

According to the invention, a preferred buffering compound is calcium carbonate. Upon reaction with an acid, calcium carbonate forms a calcium salt and the weakly acid carbonic acid ($H_2CO_3$). The carbonic acid undergoes decomposition to carbon dioxide ($CO_2$) and water ($H_2O$) according to the following reaction sequence:

$$2R-CO_2H + CaCO_3 \rightarrow (R-CO_2)_2Ca + H_2CO_3$$
$$H_2CO_3 \rightarrow CO_2 + H_2O.$$

Gaseous carbon dioxide generated from the neutralization reaction is observed to be absorbed by the surrounding aqueous medium. The solubility of gaseous $CO_2$ in water at 760 mm Hg and 37° C. is approximately 0.95 mg/ml (Merck Index, 1989). Thus, upon being generated in situ, gaseous $CO_2$ dissolves in and is eliminated from tissue fluids. In addition, free acid generation from the polymers of the invention proceeds slowly. Thus, degradation of the polymer component is the rate limiting step in the reaction, and even during the period of most rapid degradation, generation of acidic products occurs slowly. The slow rate of degradation and associated acid production gives carbon dioxide ample time to dissolve in the surrounding fluids.

The amount of calcium carbonate required to be loaded into a bioerodible polymer matrix to neutralize a given quantity of lactic and glycolytic acids can be estimated by calculating the moles of monomeric acid produced at 100% hydrolysis. For PLGA of any composition (i.e., —[—O—$CH(CH_3)$—CO—]$_x$—[O—$CH_2$—CO—]$_{(1-x)}$, where x and (1−x) are the fractions of lactide and glycolide respectively, the molecular weight of the lactide component is 72 g/mol and the molecular weight of the glycolide component is 58 g/mol), the average monomer residue molecular weight is $$72x + 58(1-x) = 14x + 58.$$

Thus, one gram of PLGA-50:50 (where x=0.5) will generate approximately 0.0154 moles of monomeric acid upon hydrolysis. Referring to the neutralization reaction above, the amount of calcium carbonate buffer needed to neutralize this quantity of acid is 0.0077 moles, or 0.77 grams (MW of $CaCO_3$=100 g/mol). Thus, the fraction of calcium carbonate buffer loaded into the polymer matrix is 43.5% by weight. Similar determinations can be calculated for other polymer and buffer combinations and are within the skills of the ordinary skilled practitioner. Other calculations may also be made, for example, calculation of the amount of buffer required to neutralize a percentage of the acid groups generated upon hydrolysis.

An appropriate buffer should have a low aqueous solubility so that it will not be rapidly lost by dissolution. The basic component of the buffer (the anion) should react easily with the protons of the acid products of hydrolysis. Letting $B^-$ represent the buffer anion and $L^-$ the lactate (or glycolic) anion, the equilibrium can be expressed as:

$$HL + B^- \rightleftharpoons L^- + HB$$

In other words, HB must be a weaker acid than HL (or $B^-$ must be a stronger base than $L^-$). These relationships may be expressed quantitatively by ionization constants of the respective acids (Ka):

$$K_aHB < K_aHL$$

Thus a viable buffer would be $CaHPO_4$ (dibasic calcium phosphate). The reaction of lactic acid with the anion $HPO_4^{-2}$ is:

$$HL + HPO_4^{-2} \rightleftharpoons L^- + H_2PO_4^-$$

The $H_2PO_4^-$ anion has an acid dissociation constant of approximately $6.31 \times 10^{-8}$ whereas the various racemates of lactic acid have dissociation constants in the range of approximately $1.38 \times 10^{-4}$ to $1.62 \times 10^{-4}$. Taking $1.5 \times 10^{-4}$ as a mean value, the equilibrium constant for the above reaction may be calculated as:

$$K_{eq} = \frac{K_a^{HL}}{K_a^{H_2PO_4^-}} = 2.4 \times 10^3$$

Thus, the equilibrium lies to the right and protons produced by ionization of lactic or glycolic acids will be removed by the buffer.

Buffers are included in the polymer in solid form preferably should have a relatively small particle size, for example, between less than 1.0 and 250 μm. Particle size reduction can be accomplished by any standard means known in the art, such as ball milling, hammer milling, air milling, etc. If buffer and polymer are to be blended by the dry mixing method (described below), the polymer particle size must also be considered. Polymers such as the PLGAs have relatively low glass transition temperatures and melting temperatures. Thus, polymer particle size reduction must be accompanied by cooling, for example using a Tekmar A-10 mill with a cryogenic attachment.

Following milling, the desired particle size range of the buffer and the polymer may be recovered by sieving through, for example, U.S. Standard sieves. Particles in the size ranges of <45, 45–90, 90–125, 125–180, 180–250 μm may be conveniently isolated.

In selection of particle size range, it is sometimes desirable to combine two or more ranges, or to use a wide range of sizes, for instance all sizes less than 250 μm. Larger particles may be preferred in some applications of the invention because larger particles take longer to be eroded by the acids and will therefore extend the useful lifetime of the buffer. In some cases particle size reduction will not be necessary, such as when commercially available precipitated calcium carbonate is used (e.g., Fisher Scientific, Inc., Catalog No. C-63).

The effectiveness of calcium carbonate in neutralizing the acid products of polymer hydrolysis depends not only on the quantity of calcium carbonate present in the matrix, but also on particle size and distribution, total surface area in contact with the polymer, and degree of solubility. Each of these parameters may be controlled by methods chosen for preparation of calcium carbonate.

Calcium carbonate exists in two major crystalline forms: calcite and aragonite. By choice of one form or the other for inclusion in the polymer, the volume fraction occupied by calcium carbonate may be adjusted within limits. Thus, for a given loading (weight percent), the aragonitic form, because of its higher specific gravity, will occupy about 9.1% less volume than will an equal weight percent of the calcitic form.

The two forms differ in their aqueous solubilities, the aragonitic form being about 46% more soluble than the calcitic form. The rate at which neutralization occurs will depend in part on the solubility of the buffering agent. Thus aragonite reacts more rapidly with a given concentration of a given acid than calcite. Thus the presence of the aragonitic form of calcium carbonate is preferred when rapid hydrolysis of the bioerodible polymer is expected. Because of its higher solubility, the aragonitic form of calcium carbonate will also be leached out of the bioerodible polymer more rapidly. Thus, it may be desirable to incorporate both forms of calcium carbonate into the buffered material.

During the preparation of calcium carbonate, reaction conditions determine the preponderance of crystal type, mean particle size, and particle size distribution. In general, rapid precipitation, high reactant concentrations, and high temperatures increase the tendency to produce aragonite. On the other hand, calcite formation is encouraged by precipitation at temperatures below 30° C. During preparation of the buffer, reaction conditions are chosen to produce the most desirable form of calcium carbonate for a particular application. The choice of reaction conditions is well known in the art and within the skills of the ordinary skilled practitioner.

In an exemplary embodiment, calcium carbonate or calcium magnesium carbonate may be precipitated by mixing an aqueous solution containing a soluble calcium salt or soluble calcium magnesium salt with another aqueous solution containing a soluble ionic carbonate. The temperature of the process is limited by the freezing or boiling points of the solutions. The temperature at which precipitation is performed determines the relative abundance of the calcite and aragonite forms. Calcite formation is favored by precipitation (crystallization) below 30° C., and aragonite formation is favored at higher temperatures.

The range of temperatures at which precipitations can be performed may be greatly extended by taking advantage of the solubility of certain calcium compounds and carbonates in solvents other than water. For example, water soluble calcium nitrate is also freely soluble in methanol, ethanol, and acetone. These solvents may be used at temperatures limited by the freezing points of the solutions. The solution freezing points will be lower than the freezing points of the pure solvents, which are, in the order given above, −95.4° C., −117.3° C., and −93.9° C. These solvents are also freely miscible with water thus allowing aqueous solutions of these solvents to be employed as solvents for the calcium or carbonate compounds. Both forms of calcium carbonate are also soluble in glycerol or glycerol and water. Glycerol has a boiling point in excess of 290° C., at which temperature it begins to decompose. Thus mixtures of glycerol and water may be used as solvents at temperatures above the boiling point of water to perform precipitation.

It should be noted that the viscosities of acetone and methanol are less than that of water, while those of ethanol and glycerol are higher. Control of solution viscosity may be achieved by performing precipitation in mixtures of water with the above solvents. Viscosity effects may also be employed in varying morphology precipitated particles. It is well known that precipitation and crystallization from solution may be markedly affected by the presence of second solvents. This phenomenon can be used to control of particle form.

Control of buffer particle size is also important in producing the materials of the invention because solubility of the buffer is affected by particle size. In general, small crystals (e.g., <1 $\mu$m) exhibit greater solubility than larger ones.

Calcination of metallic carbonates may be employed for creating highly porous particles of buffer useful in the materials of the invention. Calcination of calcium acetate at temperatures in the range 450°–700° C. produces porous calcium carbonate particles and acetone (which decomposes to $CO_2$ and $H_2O$). At higher temperatures (700°–1000° C.), calcium carbonate is further decomposed to calcium oxide and carbon dioxide. Similarly, calcination of calcium magnesium acetate in this temperature range produces a mixed calcium magnesium carbonate. Other materials suitable for calcination include formates, propionates, gluconates, lactates, and benzoates. Calcination above 700° C. produces particles with diameters of <100 $\mu$m and with porosities as high as 0.7, and surface areas of about 27 $m^2/g$. Further reduction in particle size may be accomplished by standard techniques such as grinding, air milling, etc., and sieving. Porous calcium carbonate has the advantage of presenting a large surface area to solutions of the acid products of hydrolysis; thus, the rate of neutralization is increased.

The method of calcination to produce carbonates and then metallic oxides may be applied to any salt comprising a metallic ion and a carboxylate anion. The products are a metallic carbonate and a ketone. Further, heating of the carbonate will produce a metallic oxide, carbon dioxide, and water. As shown by Steciak et al., (A. I. Ch. E. J., 41, 712–722 (1995)) calcium magnesium acetate, when calcined at 950° C., produces particles with a porosity of 0.7, and a surface area of 27 $m^2/g$.

The presence of calcium ions in the buffered device has advantages with respect to the physical properties of the device as it undergoes erosion. It has been shown that calcium ions form ionic bridges between carboxylate terminal polymer chains (Domb et al., J. Polymer Sci. A28, 973–985 (1990); U.S. Pat. No. 4,888,413 to Domb). Calcium ion bridges increase the strength of composites in which the polymer chains are terminated with carboxylate anions over similar chains terminated with hydroxyl groups of terminal glycol moieties. In an analogous manner, the polyesters comprising the family of PLGA's are expected to be strengthened by calcium bridges between carboxylate anion terminated chains.

In addition to organic or inorganic salts which can serve as buffers, polymeric buffers may also be implemented in the materials and methods of the invention. Polymeric buffers useful in the invention preferably include at least one basic group which is capable of neutralizing the acidic products generated upon hydrolysis of the bioerodible polymer. As used herein, the term "base" and "basic group" is defined as any chemical group capable of donating an electron pair. The basic groups of the polymeric buffer may be attached to substituents pendant to the polymeric buffer backbone, or may be attached directly to the polymer backbone, or may be included as part of the polymer backbone itself. The polymers serving as buffers may be stable to hydrolysis, such as "addition" or "vinyl-type" polymers, i.e., those polymers formed by polymerization of monomers containing carbon-carbon double bonds (substituted ethylenes) to form a chain of repeating units in which the repeating unit has the same composition as the monomer. Alternatively, the buffering polymers may themselves be subject to hydrolytic action, such as "condensation" or "step" polymers, i.e., those polymers formed from polyfunctional monomers with loss of material at each step. Examples of useful condensation polymers are polyesters and polyamides.

As with buffering compounds, the negative ions of the polymeric buffers act as bases which neutralize the acids produced by hydrolysis of bioerodible polymer. A generalized structure of an exemplary polymeric buffer is shown below. In the following diagram, M represents the monomeric units which form the buffer polymer backbone, and R represents a hydrogen atom, an alkyl group or an aryl group.

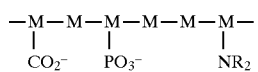

As shown in the diagram, the monomeric units M may have substituents which bear basic groups, such as carboxyl, amine, or phosphonate groups. Each monomeric unit may bear a basic group, but this is not a necessary requirement. In addition, the basic groups of a given polymeric molecule may not all be the same. As shown in the diagram above, carboxyl, amine or phosphonate groups may be used alone, or in combination. Moreover, some polymeric buffers may be synthesized from two or more monomers so that in a given polymeric buffer, the M groups differ.

Thus, according to the invention, many polymeric buffers may be selected based on properties such as buffering capacity and pKa value. An important parameter in choosing a polymeric buffer is that the pKa of the acid formed by the polymeric buffer be less than the pKa of the hydrolysis products of the bioerodible polymer. Exemplary polymeric buffers include, but are not limited to, hydrolyzable polyamines, such as poly(aspartic acid), poly(glutamic acid), poly(lysine), poly(amino-γ-benzyl glutamate); hydrolytically stable polymers (vinyl or addition polymers), such as poly (N-vinyl carbazole), poly(N-vinyl pyrrolidone), poly (acrylic acid), poly(acrylamide), or a copolymer based on acrylic acid, such as

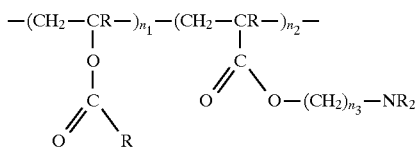

where R=H, alkyl, or aryl, (R groups need not be identical). In copolymers, such as copolymers of acrylic acid, the residue monomer units forming the backbone may be distributed randomly or may occur in sequential blocks (random or block copolymers). Hydrolyzable polyesters of the general structure

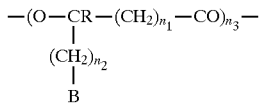

may also be used. In the structures shown above, R=H, alkyl, or aryl; $n_1$ and $n_2 \geq 0$; $n_3 \geq 3$; B=a basic group, such as $-CO_2-$, $-NR_2$ or $-PO_3R-$.

In an alternative embodiment, the basic group of the polymeric buffer may be covalently bonded within the monomeric unit. An example of this type of polymeric buffer is poly(ethylamine)-$(CH_2-CH_2-NH)_n-$.

Another class of buffer compounds useful in the invention are compounds which, on exposure to water, hydrolyze to form a base as one reaction product. This generated base is then free to react with the acidic products produced upon hydrolysis of the bioerodible polymer.

In one embodiment, compounds such as aryl and alkyl carbamic acids may be implemented to generate the basic compounds that act as buffers. The hydrolysis reaction which results in base generation is:

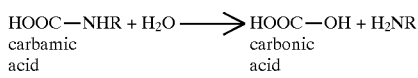

The carbonic acid generated during the reaction is in equilibrium with carbon dioxide and water:

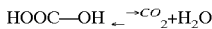

The basic product $H_2NR$ reacts with the acid products of bioerodible polymer hydrolysis in a neutralization reaction. In one embodiment, the hydrolysis products of poly(lactide-co-glycolide) (hereinafter designated as HL) may be neutralized by the generated base:

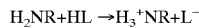

In an alternative embodiment, imines may also be used to generate bases on hydrolysis according to the general equation:

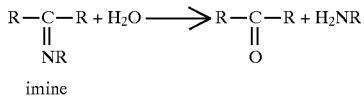

The groups labelled R above may be a hydrogen atom, an alkyl group, or an aryl group.

Following protonation of the imine nitrogen, hydrolysis proceeds by nucleophilic attack by water at the carbon atom of the C=N bond. This process is facilitated by electron withdrawing groups attached to the nitrogen. Such substituents would thus increase the rate of hydrolysis. Conversely, the rate of hydrolysis would be diminished by electron donating substituents on the carbon and an electron withdrawing group on the nitrogen. Bulky groups, such as long alkyl substituents would tend to offer steric hindrance to the approach of the water molecules and thus would suppress the hydrolysis rate. Accordingly, by appropriate choice of R, the rate of hydrolysis of the imine may be either increased or decreased. This characteristic of base generating compounds is advantageous in that the rate of hydrolysis of the base generator may be selected to correlate to the rate of hydrolysis of the bioerodible polymer. Thus, in a given period of time, the quantity of base formed from the base generating compound will be equivalent to the quantity of acidic products formed by bioerodible polymer hydrolysis, and the stoichiometry of the reaction will be in the correct proportions to neutralize the appropriate amount of acid to maintain the pH within the desired range.

Several methods may be used to incorporate the buffer into the polymer. These methods include solution casting coupled with solvent evaporation, dry mixing, incorporating the buffer into a polymer foam, and the polymer melt method.

Method 1. Solution Casting-Solvent Evaporation

This method may be used with buffers which are either soluble or insoluble in the solvent. The bioerodible polymer is dissolved in any suitable volatile solvent, such as acetone, tetrahydrofuran (THF), or methylene chloride. The buffer, which may be soluble or insoluble in this solvent, is added to give the final desired ratio of polymer to buffer. If particle size reduction of the buffer is necessary, it may be accomplished by ball milling the suspension of buffer in the polymer solution. In contrast, if the buffer is soluble in the chosen solvent, particle size reduction at any stage is not necessary.

The suspension or co-solution is cast as a film on a glass or other inert surface, and the solvent is removed by air drying. Residual solvent remaining in the film may be further removed by subjecting the film to vacuum drying at elevated temperatures. As an example, if calcium carbonate is to be used as a buffering compound and it is desired to neutralize 50% of the acid formed by hydrolysis of PLGA-50:50, the buffer content of the composition should be 27.8%.

In an exemplary embodiment, to prepare 50 grams of composite, 36.1 grams of PLGA-50:50 are dissolved in approximately 250 ml of tetrahydrofuran, and 13.9 grams of calcium carbonate of the desired particle size range is added to the solution mixture. After distributing the calcium carbonate homogeneously by mixing, the suspension is dried to a film as described above.

The resulting film may be processed by compaction under high pressure, extruded through a die, injection molded, or other method known in the art. Further definition of the final shape may be accomplished at this point by any desirable machining process, such as lathing.

Method 2. Dry-Mixing

A polymer of appropriate particle size range is mixed with the buffer, also of chosen particle size range, in proportions to give the desired stoichiometric buffering capacity. The dry mixture is thoroughly blended by rotating the mixture in a ball mill jar from which the grinding balls have been omitted, or other suitable mixing device. The blended mixture may then be processed by compaction, extrusion, injection molding, etc., as described above.

Method 3. Incorporating the Buffer into a Polymer Foam

This method deposits the buffer as microcrystals within the pores of a foamed polymer. An open celled polymer foam of controlled density may be formed by lyophilization of a polymer solution as described in U.S. Pat. No. 5,456,917 to Wise et al., the whole of which is incorporated by reference herein. For example, open celled PLGA-85:15 foams (i.e., foams with 85% lactide and 15% glycolide by weight) with different morphologies are created by lyophilization of frozen solutions of the polymer from either benzene or glacial acetic acid. The density and void volume of the foam is a function of the initial polymer solution as shown in TABLE 1.

TABLE 1

FOAM DENSITY AS A FUNCTION OF SOLUTION CONCENTRATION

| Concentration of solution, mg/ml | Density of Foam, $mg/cm_3$ |
|---|---|
| 30.0 | 43.0 |
| 40.0 | 60.1 |
| 45.0 | 65.0 |
| 50.0 | 70.1 ± 0.9 |
| 66.7 | 87.5 |

In this method, buffers which are soluble in a solvent which does not dissolve the polymer foam are preferred, such as water soluble buffers or low molecular weight alcohols, such as ethanol. The weight fraction of the buffer in the polymer/buffer composite, f, will depend on both absolute density of the polymer, $d_p$, the density of the foam, $d_f$, and the concentration of the buffer in the solvent, C. This dependency is given by the loading equation:

$$f=[1+d_f d_p/C(d_p-d_f)]^{-1}$$

TABLE 2 shows loading of PLGA-85:15 foams prepared from acetic acid solutions with the anti-tuberculosis drug isoniazid dissolved in water. Results of these loading experiments are given in TABLE 2.

TABLE 2

INH CONTENT (WEIGHT PERCENT) IN FOAMS AS A FUNCTION OF INH SOLUTION CONCENTRATION AND FOAM DENSITY

| INH Soln. | Foam Density, $mg/cm^3$ | | |
|---|---|---|---|
| Conc., mg/ml | 43.0 | 70.1 | 87.5 |
| 13.0 | 20.0$^a$(22.8$^b$) | — | — |
| 21.5 | 26.5 (32.8) | — | — |
| 29.4 | 35.0 (44.0) | — | — |
| 5.1 | — | 6.0 (6.5) | — |
| 11.5 | — | 12.0 (13.6) | — |
| 25.0 | — | 24.7 (25.5) | — |
| 10.0 | — | — | 9.0 (9.8) |
| 21.5 | — | — | 18.4 (18.9) |
| 39.5 | — | — | 28.0 (30.0) |

$^a$Measured values of loading.
$^b$Loadings as predicted by the loading equation.

A buffer solution comprising a chosen buffer in a suitable solvent is forced into the pores of the open celled foam by repeated cycles of evacuation (degassing) and repressurization (by emitting air at atmospheric pressure or higher). After the foam has been impregnated with the buffer solution, excess solution is drained off and the saturated foam is subjected to a second lyophilization to remove the solvent. Following this loading process, the polymer/buffer composite may be processed as described above.

Method 4. Polymer Melt

A known weight of the buffer is incorporated by mixing into a known weight of a suitable melted polymer. A quantity of polymer is heated to a temperature above its melting point, and a suitable buffer is blended into the melted polymer. The resulting polymer/buffer composite is solidified by cooling, and may be processed as described above, or ground and sieved prior to processing.

In some applications, it may be desirable to protect the buffering compound, for example, during processing according to the melt method, or to make the buffering compound available at the later stages of polymer degradation. In such cases, it is desirable to coat the buffering compound particles with a material that degrades at a slower rate than the material chosen for the fixation devices. Thus, the buffering compound is exposed only after the body of the device and the coating material have partially degraded. Exemplary materials used to coat the buffering compound particles include high molecular weight poly(L-lactide) or poly($\epsilon$-caprolactone).

The particles of buffering compound may be coated with the protective material by any method that coats particles, such as spray coating with a solution of protecting polymer or micro-encapsulation. Alternatively, a chosen protective polymer may be made in a melted state and buffer particles are added. The melt is cooled and ground and milled to the desired particle size range. Alternatively, the buffering compound may be added to a solution of the protective polymer and removing the solvent by evaporation. The dried mass is compacted in a mold under high pressure and grinding or milling the compacted mass to the appropriate particle size range.

Although PLGA polymers are used in the preceding examples, one of ordinary skill in the art will appreciate that other polymers, such as polydioxanone, poly($\epsilon$-caprolactone); polyanhydrides; poly(ortho esters); copoly (ether-esters) ; polyamides; polylactones; poly(propylene fumarates); and combinations thereof, may be similarly processed according to the methods of the invention. Moreover, selection of a particular polymer is based primarily on the known properties of the polymer such as the degree of cross-linking, polymer strength, polymerization rate, rate of hydrolytic degradation, etc. One of ordinary skill in the art may take these and/or other properties into account in selecting a particular polymer for a particular application. Thus, such a selection of a particular polymer is within the skills of the ordinary skilled practitioner.

Having showed the preferred embodiments, those skilled in the art will realize many variations are possible which will still be within the spirit and scope of the claimed invention. Therefore, it is the intention to limit the invention only as indicated by the scope of the claims.

We claim:

1. A bioerodible implantable material, comprising:
    a bioerodible polymer, said bioerodible polymer producing acidic products upon hydrolytic degradation; and
    a buffer in sufficiently high concentration so as to buffer said acidic products within a pH range within which physiological irritation, inflammation, and swelling (sterile abscess formation) caused by said unbuffered acidic products in vivo is prevented or ameliorated.

2. The bioerodible implantable material of claim 1, wherein said bioerodible polymer is selected from the group consisting of polydioxanone, poly(ε-caprolactone), polyanhydride, poly(ortho ester), copoly(ether-ester), polyamide, polylactone, poly(propylene fumarate), and combinations thereof.

3. The bioerodible implantable material of claim 1, wherein said bioerodible polymer comprises poly(lactide-co-glycolide) with a lactide to glycolide ratio in the range of 0:100% to 100:0% inclusive.

4. The bioerodible implantable material of claim 1, wherein said buffer is the salt of an inorganic acid.

5. The bioerodible implantable material of claim 1, wherein said buffer is the salt of an organic acid.

6. The bioerodible implantable material of claim 1, wherein said buffer is a polymer comprising at least one basic group.

7. The bioerodible implantable material of claim 6, wherein said polymer comprising at least one basic group is selected from the group consisting of hydrolyzable polyamines, hydrolyzable polyesters, vinyl polymers, and copolymers of acrylic acid.

8. The bioerodible implantable material of claim 6, wherein said at least one basic group is covalently bonded within said polymer.

9. The bioerodible implantable material of claim 1, wherein said buffer is a compound which, on exposure to water, hydrolyzes to form a base.

10. The bioerodible implantable material of claim 9, wherein the quantity of said base generated upon hydrolysis is equivalent to the quantity of said acidic products formed by said bioerodible polymer hydrolysis.

11. The bioerodible implantable material of claim 1, wherein said buffer is selected from the group consisting of carbonates, phosphates, acetates, succinates, and citrates.

12. The bioerodible, implantable material of claim 1, wherein said buffer is a calcium salt.

13. The bioerodible, implantable material of claim 1, wherein said buffer is calcium carbonate.

14. The bioerodible implantable material of claim 1, wherein the parent acid of said buffer has an acid dissociation constant that is smaller than the acid dissociation constant of said acidic products.

15. The bioerodible implantable material of claim 1, wherein said buffer has a hydrolysis constant that is greater than the hydrolysis constant of said acidic products.

16. The bioerodible implantable material of claim 1, wherein said pH range is 6.8–7.4.

17. A method of making a buffered bioerodible, implantable material, comprising the steps of:
    dissolving a bioerodible polymer in a solvent, said bioerodible polymer producing acidic products upon hydrolytic degradation;
    mixing a buffer with said dissolved bioerodible polymer, said buffer present in sufficently high concentration so as to buffer said acidic products within a pH range within which physiological irritation, inflammation, and swelling (sterile abscess formation) caused by said unbuffered acidic products in vivo is prevented or ameliorated;
    casting said mixture; and
    evaporating said solvent of said mixture to produce a buffered bioerodible implantable material.

18. The method of claim 17, wherein said bioerodible polymer is selected from the group consisting of polydioxanone, poly(ε-caprolactone), polyanhydride, poly(ortho ester), copoly(ether-ester), polyamide, polylactone, poly(propylene fumarate), and combinations thereof.

19. The method of claim 17, wherein said bioerodible polymer comprises poly(lactide-co-glycolide) with a lactide to glycolide ratio in the range of 0:100% to 100:0% inclusive.

20. The method of claim 17, wherein said buffer is the salt of an inorganic acid.

21. The method of claim 17, wherein said buffer is the salt of an organic acid.

22. The method of claim 17, wherein said buffer is a polymer comprising at least one basic group.

23. The method of claim 17, wherein said buffer is a compound which, on exposure to water, hydrolyzes to form a base.

24. The method of claim 17, further comprising the step of milling said buffer in said polymer solution.

25. The method of claim 17, further comprising the step of processing said buffered bioerodible implantable material into a desired form.

26. The method of claim 17, further comprising the step of coating said buffer with a polymeric material that degrades at a slower rate than PLGA.

27. The method of claim 17, further comprising the steps of:
    providing a first solution comprising a soluble calcium salt;
    providing a second solution comprising a soluble ionic carbonate;
    mixing said first solution and said second solution to form a calcium carbonate precipitate; and
    collecting said calcium carbonate precipitate for use as said buffer.

28. The method of claim 27, wherein said calcium carbonate precipitate comprises calcite and aragonite.

29. The method of claim 17, further comprising the steps of:
    providing a salt comprising a metal ion and a carboxylate ion; and
    combusting said salt to form said buffer.

30. The method of claim 29, wherein said combusting step takes place at temperatures between 450° and 1000° C., inclusive.

31. A method for making a buffered bioerodible implantable PLGA material, comprising the steps of:

providing bioerodible polymer particles having a specific size, said bioerodible polymer producing acidic products upon hydrolytic degradation;

providing buffer particles having a specific size, said buffer particles comprising a buffer present in sufficiently high concentration so as to buffer said acidic products within a pH range within which physiological irritation, inflammation, and swelling (sterile abscess formation) caused by said unbuffered acidic products in vivo is prevented or ameliorated; and mixing said bioerodible polymer particles and said buffer particles in a predetermined proportion.

32. The method of claim 31, wherein said bioerodible polymer particles comprise poly(lactide-co-glycolide) with a lactide to glycolide ratio in the range of 0:100% to 100:0% inclusive.

33. The method of claim 31, wherein said buffer is the salt of an inorganic acid.

34. The method of claim 31, wherein said buffer is the salt of an organic acid.

35. The method of claim 31, wherein said buffer is a polymer comprising at least one basic group.

36. The method of claim 31, wherein said buffer is a compound which, on exposure to water, hydrolyzes to form a base.

37. The method of claim 31, further comprising the step of processing said buffered bioerodible implantable material into a desired form.

38. The method of claim 31, further comprising the step of coating said buffer particles with a polymeric material that degrades at a slower rate than PLGA.

39. The method of claim 31, further comprising the steps of:

providing a first solution comprising a soluble calcium salt;

providing a second solution comprising a soluble ionic carbonate;

mixing said first solution and said second solution to form a calcium carbonate precipitate; and collecting said calcium carbonate precipitate for use as said buffer particles.

40. The method of claim 39, wherein said calcium carbonate precipitate comprises calcite and aragonite.

41. The method of claim 31, further comprising the steps of:

providing a salt comprising a metal ion and a carboxylate ion; and combusting said salt to form said buffer.

42. The method of claim 41, wherein said combusting step takes place at temperatures between 450° and 1000° C., inclusive.

43. A method for making a buffered bioerodible implantable material, comprising the steps of:

providing an open celled bioerodible foam polymer of controlled density, said bioerodible foam polymer producing acidic products upon hydrolytic degradation;

providing a buffer dissolved in a solvent, said foam polymer not soluble in said solvent, present in sufficiently high concentration so as to buffer said acidic products within a pH range within which physiological irritation, inflammation, and swelling (sterile abscess formation) caused by said unbuffered acidic products in vivo is prevented or ameliorated;

loading said buffer compound dissolved in said solvent into said PLGA foam polymer; and freeze drying said buffer loaded foam polymer to remove said solvent.

44. The method of claim 43, further comprising the step of processing said buffered bioerodible implantable material into a desired form.

45. The method of claim 43, further comprising the step of coating said buffer particles with a polymeric material that degrades at a slower rate than PLGA.

46. The method of claim 43, wherein said bioerodible polymer comprises poly(lactide-co-glycolide) with a lactide to glycolide ratio in the range of 100:0 to 0:100 inclusive.

47. The method of claim 43, wherein said buffer is the salt of an inorganic acid.

48. The method of claim 43, wherein said buffer is the salt of an organic acid.

49. The method of claim 43, wherein said buffer is a polymer comprising at least one basic group.

50. The method of claim 43, wherein said buffer is a compound which, on exposure to water, hydrolyzes to form a base.

51. A method for making a buffered bioerodible implantable material, comprising the steps of:

providing a bioerodible polymer having a first melting temperature, said bioerodible polymer producing acidic products upon hydrolytic degradation;

providing buffer particles comprising buffer material coated with a protective polymer, said protective polymer having a second melting temperature, said second melting temperature greater than said first melting temperature, said buffer particles comprising a buffer present in sufficiently high concentration so as to buffer said acidic products within a pH range within which physiological irritation, inflammation, and swelling (sterile abscess formation) caused by said unbuffered acidic products in vivo is prevented or ameliorated;

heating said bioerodible polymer to a temperature between said first melting temperature and said second melting temperature;

mixing said heated bioerodible polymer and said coated buffer particles; and cooling said mixture.

52. The method of claim 51, further comprising the step of processing said buffered bioerodible implantable material into a desired form.

53. The method of claim 51, wherein said bioerodible polymer comprises poly(lactide-co-glycolide) with a lactide to glycolide ratio in the range of 100:0 to 0:100 inclusive.

54. The method of claim 51, wherein said buffer is the salt of an inorganic acid.

55. The method of claim 51, wherein said buffer is the salt of an organic acid.

56. The method of claim 51, wherein said buffer is a polymer comprising at least one basic group.

57. The method of claim 51, wherein said buffer is a compound which, on exposure to water, hydrolyzes to form a base.

58. The method of claim 51, further comprising the steps of:

providing a first solution comprising a soluble calcium salt;

providing a second solution comprising a soluble ionic carbonate;

mixing said first solution and said second solution to form a calcium carbonate precipitate; and collecting said calcium carbonate precipitate for use as said buffer.

59. The method of claim 58, wherein said calcium carbonate precipitate comprises calcite and aragonite.

60. The method of claim 51, further comprising the steps of:

provided a salt comprising a metal ion and a carboxylate ion; and combusting said salt to form said buffer material.

61. The method of claim 60, wherein said combusting step takes place at temperatures between 450° and 1000° C., inclusive.

* * * * *

UNITED STATES PATENT AND TRADEMARK OFFICE
CERTIFICATE OF CORRECTION

PATENT NO. : 5,817,328
DATED : October 6, 1998
INVENTOR(S) : Joseph D. Gresser et al.

It is certified that error appears in the above-identified patent and that said Letters Patent is hereby corrected as shown below:

Column 5,
Lines 24-25, reads as follows:

should read

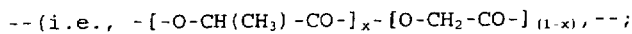

Line 52, reads as follows:

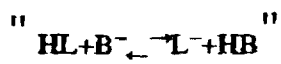

should read

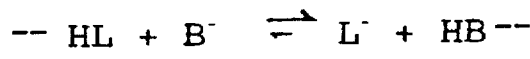

Line 59, "KaHB<KaHL" should read -- $Ka^{HB} < Ka^{HL}$ --;
Line 64, reads as follows:

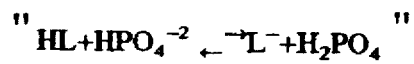

should read

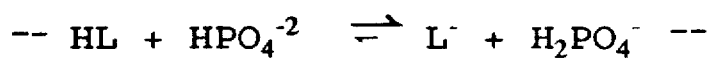

Column 9,
Line 40, "—$CO_2$-, —$NR_2$, or —$PO_3R$- ." should read -- $-CO_2^-$, $-NR_2$, or $-PO_3R^-$. --;
Line 61, reads as follows:

should read

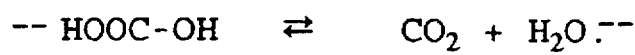

UNITED STATES PATENT AND TRADEMARK OFFICE
CERTIFICATE OF CORRECTION

PATENT NO. : 5,817,328
DATED : October 6, 1998
INVENTOR(S) : Joseph D. Gresser et al.

It is certified that error appears in the above-identified patent and that said Letters Patent is hereby corrected as shown below:

Column 11,
Line 62, "$f=[1+d_f d_p/C(d_p-d_f)]^{31\ 1}$" should read -- $f=[1+ d_f d_p/C(d_p-d_f)]^{-1}$ --.

Signed and Sealed this

Seventh Day of May, 2002

Attest:

JAMES E. ROGAN
*Attesting Officer*     *Director of the United States Patent and Trademark Office*